(12) United States Patent
Pennefather et al.

(10) Patent No.: US 9,465,858 B2
(45) Date of Patent: Oct. 11, 2016

(54) SYSTEMS AND METHODS FOR AUTHENTICATING AND AIDING IN INDEXING OF AND SEARCHING FOR ELECTRONIC FILES

(75) Inventors: Peter Pennefather, Toronto (CA); West Suhanic, Toronto (CA)

(73) Assignee: GDIAL INC., Toronto (CA)

( * ) Notice: Subject to any disclaimer, the term of this patent is extended or adjusted under 35 U.S.C. 154(b) by 168 days.

(21) Appl. No.: 14/123,284

(22) PCT Filed: Jun. 1, 2012

(86) PCT No.: PCT/CA2012/000515
§ 371 (c)(1),
(2), (4) Date: Dec. 2, 2013

(87) PCT Pub. No.: WO2012/162803
PCT Pub. Date: Dec. 6, 2012

(65) Prior Publication Data
US 2014/0122491 A1    May 1, 2014

Related U.S. Application Data

(60) Provisional application No. 61/492,835, filed on Jun. 3, 2011.

(51) Int. Cl.
*G06F 7/00* (2006.01)
*G06F 17/30* (2006.01)
*G06F 19/00* (2011.01)
*G06F 21/64* (2013.01)

(52) U.S. Cl.
CPC ... *G06F 17/30598* (2013.01); *G06F 17/30321* (2013.01); *G06F 19/321* (2013.01); *G06F 19/322* (2013.01); *G06F 21/645* (2013.01)

(58) Field of Classification Search
CPC .............. G06F 17/30598; G06F 17/30321; G06F 21/645; G06F 19/321; G06F 19/322; G06F 11/1435; G06F 11/3086; G06F 17/301; G06F 17/30525; G06F 17/30722; G06F 17/30997
USPC .................. 707/771, 776, 737, 999.107
See application file for complete search history.

(56) References Cited

U.S. PATENT DOCUMENTS

| | | | |
|---|---|---|---|
| 7,613,727 B2* | 11/2009 | Visharam et al. | |
| 8,036,475 B2* | 10/2011 | Boliek et al. | 382/233 |
| 8,156,123 B2* | 4/2012 | Tribble et al. | 707/739 |
| 2002/0065844 A1* | 5/2002 | Robinson et al. | 707/500 |
| 2002/0194480 A1* | 12/2002 | Nagao | 713/176 |

(Continued)

*Primary Examiner* — Mohammed R Uddin
(74) *Attorney, Agent, or Firm* — Perry + Currier Inc.

(57) ABSTRACT

According to some aspects there is provided a system, method and a device for generating at least one electronic file. The method includes receiving primary data for at least one page to be included in an electronic file; receiving metadata associated with the primary data, the metadata comprising a plurality of tags and corresponding tag values associated therewith; generating a globally unique identifier associated with the page based upon the primary data and the metadata associated therewith; storing the globally unique identifier as a tag value for a unique identifier tag in the metadata associated with that page; generating the at least one page for the file, the at least one page comprising the page data and the metadata including the globally unique identifier; if the at least one page includes a plurality of pages, repeating above to generate a plurality of the pages for the electronic file; and storing the file comprising the at least one generated page in a data storage device.

21 Claims, 6 Drawing Sheets

(56) References Cited

U.S. PATENT DOCUMENTS

| | | |
|---|---|---|
| 2003/0081145 A1* | 5/2003 | Seaman et al. ............... 348/460 |
| 2003/0195863 A1* | 10/2003 | Marsh .............................. 707/1 |
| 2004/0076345 A1* | 4/2004 | Olszak et al. ................ 382/309 |
| 2004/0114813 A1* | 6/2004 | Boliek et al. ................. 382/233 |
| 2004/0177319 A1* | 9/2004 | Horn .......................... 715/501.1 |
| 2006/0251338 A1* | 11/2006 | Gokturk et al. .............. 382/305 |
| 2007/0073688 A1* | 3/2007 | Fry .................................. 707/6 |
| 2007/0118540 A1* | 5/2007 | Guo ............................. 707/100 |
| 2007/0127833 A1* | 6/2007 | Singh ........................... 382/254 |
| 2007/0266252 A1 | 11/2007 | Davis et al. |
| 2007/0299806 A1* | 12/2007 | Bardsley et al. ................. 707/1 |
| 2008/0137688 A1* | 6/2008 | Walsh ........................... 370/498 |
| 2008/0222201 A1* | 9/2008 | Chen et al. ................ 707/104.1 |
| 2009/0006474 A1* | 1/2009 | Richardson et al. ...... 707/104.1 |
| 2009/0157987 A1 | 6/2009 | Barley et al. |
| 2009/0182577 A1* | 7/2009 | Squilla et al. .................... 705/2 |
| 2009/0248672 A1* | 10/2009 | McIntire et al. .................. 707/5 |
| 2010/0037161 A1* | 2/2010 | Stading et al. ............... 715/764 |
| 2010/0063961 A1* | 3/2010 | Guiheneuf et al. ........... 707/622 |
| 2010/0293190 A1* | 11/2010 | Kaiser et al. ................. 707/769 |
| 2011/0103699 A1* | 5/2011 | Ke et al. ....................... 382/209 |
| 2011/0106782 A1* | 5/2011 | Ke et al. ....................... 707/706 |
| 2011/0131081 A1* | 6/2011 | Nielsen et al. .............. 705/7.42 |
| 2011/0178996 A1* | 7/2011 | Pendlebury et al. ......... 707/692 |
| 2011/0295775 A1* | 12/2011 | Wang et al. .................... 706/12 |
| 2012/0030575 A1* | 2/2012 | Cok .............................. 715/738 |
| 2012/0203859 A1* | 8/2012 | Krzyzanowski .............. 709/217 |
| 2012/0249575 A1* | 10/2012 | Krolczyk et al. ............. 345/619 |
| 2013/0014007 A1* | 1/2013 | Kopp et al. ................... 715/243 |

* cited by examiner

SYSTEMS AND METHODS FOR AUTHENTICATING AND AIDING IN INDEXING OF AND SEARCHING FOR ELECTRONIC FILES

TECHNICAL FIELD

The present disclosure relates to information management systems and methods, and in particular systems and methods for managing and authenticating electronic files.

INTRODUCTION

In various sectors including the medical community, diagnostic information is used to help understand the underlying causes of conditions in order to support various forms of decision-making. A diagnostic test probes or examines a situation in a specific manner and generates primary data about that situation. For example, primary data may include recorded or captured digital images or video, digital audio, or various combinations thereof.

In addition to the primary diagnostic data, there may also be secondary data, which is sometimes referred to as metadata, which contains information related to and about the primary data. Generally, the primary data comprises information dependent on a target subject while the metadata comprises data which provides a context for interpreting the primary data. For example, if the primary data is an x-ray of a patient, the metadata may include referring physician's information, target of the x-ray (e.g. left ankle), type of imaging machine used, reviewing physician's diagnosis and so on.

Generally, both the primary data and metadata are recorded on a computer readable medium as electronic files. In many cases, these electronic files are composed of file envelopes that bind various types of data together with one or more pages assigned to a single file name. Based on the nature of the primary data, the electronic file pages and the file envelope in which they are found may be formatted to be compliant with one or more industry standards. Examples of current industry standards for digital electronic file formats include: the Tagged Image File Format (TIFF), the Moving Pictures Expert Group (MPEG), the Digital Image and Communication in Medicine (DICOM) and the Portable Document Format (PDF).

Using electronic file to store diagnostic data provides many advantages. For example, electronic files can be conveniently reproduced, transmitted over networks, indexed, and compared to others, and so on. Such advantages contribute to the prevalence of digital diagnostic data storage in various industries and communities ranging from medical imaging in healthcare settings to target acquisition in battlefield settings or in evaluating security threats. Electronic file may be used to facilitate sharing of information necessary for individuals and/or groups operating in those settings to diagnose situations so as to coordinate activities and act concertedly as well as to record what has happened for future reference. As the number and complexity of diagnostic events increase the amount of primary data and metadata that is indexed and searched also increases. As such, more and more resources are necessary to manage and store such information.

In some cases, the format of the metadata may not be the same as the primary data. This may result in the primary data and the metadata being stored in multiple files of different formats. This may lead to separation of the primary data from the metadata, and increases the risk of having to interpret the primary data without reference to the metadata.

In some cases, the primary data may include a series of test results and it may be preferable to interpret each individual test result in light of other results in the same series. For example, the primary data may be a series of digital x-ray images of a limb taken at various time periods to monitor recovery. In such cases, it may not be preferable to store the multiple test results as multiple independent files as this may lead to various test results being stored in different locations, and increases the risk of having to interpret the primary data without reference to other primary data in the series. There is also a need to record the position and relative purpose and outcomes of a particular diagnostic event, with all of its associated metadata, within a series or a set of series.

In some cases, multiple copies of the files and their contents may be generated for various reasons. Having multiple copies provides a challenge to track the source of each copy so as to verify that each copy is an accurate reproduction of the original data. Proving that an electronic file element being accessed in making a decision has not been altered is an important issue in medical, legal, industrial, military, security, and regulatory practice. It is also an important issue in scientific research and commercial development where chains of evidence guide information synthesis, knowledge creation and knowledge elaboration. As such, it is generally desirable to provide a system that can provide assurance that contents of the copied electronic file element remains true to the original.

The integrity of the primary data and/or metadata is also a concern to users of the electronic file elements. For example, in medical diagnostics, it is advantageous to be able to assure medical professionals and patients that both the primary data and metadata in an electronic file that they are referring to have not been tampered with or corrupted. This is also advantageous in other industries where the integrity of the contents of the electronic files is a concern. For example, a judge or a jury viewing a forensic image taken from a crime scene needs to be assured that digital images presented as evidence are the original un-edited images. Military and security decision makers need to be assured that target images have not been altered. Consumers need to be assured that the digital image of a manufactured product that they intend to purchase over the Internet corresponds to the product that they desire to acquire.

In many cases the user has evidence or reason to believe that a series of diagnostic information has been recorded in an electronic file for subsequent use in making a decision about the dilemmas mentioned above. The user can then use a search process or query an indexed database to retrieve the name and location of that file and use those coordinates to access the file's content. However, it may be challenging to verify that that this information is authentic.

Accordingly, there is a need for systems and methods that address one or more of the challenges found in existing electronic files.

SUMMARY

According to some aspects, there is provided a computer implemented method for generating at least one electronic file. The method includes: receiving primary data for at least one page to be included in an electronic file; receiving metadata associated with the primary data, the metadata comprising a plurality of tags and corresponding tag values associated therewith; generating a globally unique identifier associated with the page based upon the primary data and the metadata associated therewith; storing the globally unique identifier as a tag value for a unique identifier tag in the metadata associated with that page; generating the at least one page for the file, the at least one page comprising the page data and the metadata including the globally unique identifier; if the at least one page includes a plurality of pages, repeating above to generate a plurality of the pages for the electronic file; and storing the file comprising the at least one generated page in a data storage device.

According to some aspects, the method further includes establishing a repository storing a plurality of the globally unique identifiers and providing access to the globally unique identifiers stored in the repository.

According to some aspects, the method further includes establishing a authenticated connection to a data storage device after at least one of the globally unique identifiers is generated, and providing the at least one of the globally unique identifiers to the data storage device to establish the repository.

According to some aspects, the stored electronic file is compliant with at least one of the following file formats comprising TIFF format including 32-bit LibTIFF standard and 64 bit BigTIFF standard; JPEG, PNG; JPEG2000; FITS; and DICOM.

According to some aspects, when at least one of the tags includes a semantic tag name in a format permitting a complex character set, the method further includes generating an alpha-numeric identifier for the semantic-tag name, the alpha-numeric identifier being specified in a less-complex character set including alphabets and numbers, and storing the generated alpha-numeric identifier as a tag value for an alpha-numeric identifier tag in the metadata including the semantic tag name.

According to some aspects, the alpha-numeric identifiers for the semantic-name tags are generated using a same function that is used to generate the globally unique identifiers.

According to some aspects, the primary data for at least one of the pages includes a placeholder anchor, and the metadata associated with the primary data includes meaningful data such that a file format is preserved regardless of the content of the primary data.

According to some aspects, the method further includes receiving annotations about the page data and location within the page data that the annotations are associated with, and storing the received annotations and the associated location for the annotations as a tag value corresponding to an annotations tag.

According to some aspects, the method further includes generating a database based upon at least one electronic file and the globally unique identifiers associated with the pages within the electronic file.

According to some aspects, there is provided a computer-implemented authentication method. The method includes: providing an authentication server with access to a repository storing a plurality of verified globally unique identifiers, each of the verified globally unique identifiers having been generated based upon primary data and metadata associated with at least one page for an electronic file, and provided to the repository from an authenticated source; and receiving an authentication request comprising an unverified value purporting to be a globally unique identifier; determining whether the repository includes a verified globally unique identifier that matches the unverified value; and responding to the authentication request based whether a matching verified unique identifier is located in the repository.

According to some aspects, when at least one of the unverified values is associated with a product, the method further includes: identifying expected product data that is associated with the matching verified unique identifier wherein when the matching verified unique identifier is located; and providing the expected product data in response to the authentication request.

According to some aspects, there is provided a device for generating at least one electronic file. The device includes at least one processor configured to: receive primary data for at least one page to be included in an electronic file; receive metadata associated with the primary data, the metadata comprising a plurality of tags and corresponding tag values associated therewith; generate a globally unique identifier associated with the page based upon the primary data and the metadata associated therewith; store the globally unique identifier as a tag value for a unique identifier tag in the metadata associated with that page; generate the at least one page for the file, the at least one page comprising the page data and the metadata including the globally unique identifier; if the at least one page includes a plurality of pages, repeat steps (a) to (e) to generate a plurality of the pages for the electronic file; and store the file comprising the at least one generated page in a data storage device.

According to some aspects, there is provided an authentication system including at least one repository, at least one file source, and at least one authentication server. The at least one file source includes at least one processor configured to: receive primary data for at least one page to be included in an electronic file, receive metadata associated with the primary data, the metadata comprising a plurality of tags and corresponding tag values associated therewith, generate a globally unique identifier associated with the page based upon the primary data and the metadata associated therewith, store the globally unique identifier as a tag value for a unique identifier tag in the metadata associated with that page, generate the at least one page for the file, the at least one page comprising the page data and the metadata including the globally unique identifier, if the at least one page includes a plurality of pages, repeat steps (a) to (e) to generate a plurality of the pages for the electronic file, and store the file comprising the at least one generated page in the repository. The at least one authentication server has a processor configured to: receive an authentication request comprising an unverified value purporting to be a globally unique identifier, determine whether the repository includes a verified globally unique identifier that matches the unverified value, and respond to the authentication request based whether a matching verified unique identifier is located in the repository.

BRIEF DESCRIPTION OF THE DRAWINGS

The drawings included herewith are for illustrating various examples of methods and apparatus of the present specification and are not intended to limit the scope of what is taught in any way. In the drawings.

DETAILED DESCRIPTION OF SOME EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers systems each comprising at least one processor, a data storage system (including volatile and/or non-volatile memory and/or storage elements), at least one input device, and at least one output device. For example and without limitation, the programmable computers may be a mainframe computer, server, embedded computer, personal computer, laptop, personal data assistant, cellular telephone, or computers in a cloud computing environment. Program code is applied to input data to perform the functions described herein and generate output information. The output information is applied to one or more output devices or a data storage device in a known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM, solid state disk or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Figure 1:
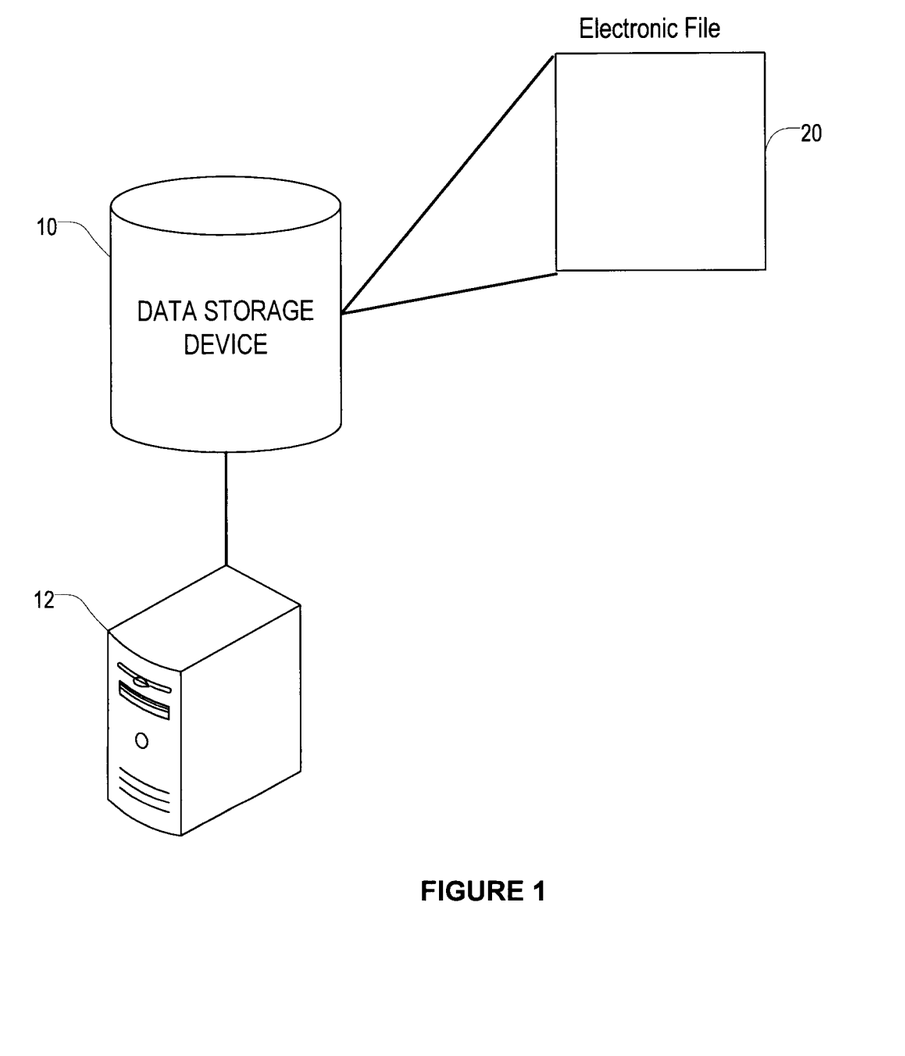
FIG. 1 is a schematic diagram illustrating a data storage device having at least one electronic file according to some embodiments.

Referring to FIG. 1, illustrated therein is a data storage device 10 having an electronic file 20 according to one embodiment of the invention. The data storage device 10 may be a computer hard disk drive or any other type of computer readable medium. The data storage device 10 has at least one electronic file such as the electronic file 20.

The data storage device 10 is coupled to the electronic device 12. The electronic device 12 has a processor which is configured to generate the electronic file 20. The electronic device 12 may be a source for the data stored in the file. For example, the device 12 may process data generated by an imaging device such as a digital camera and/or a medical imaging device to generate the electronic file 20. The device 12 may process output from other tools such as image processing tools, PDF generating tools, word-processing tools to generate the electronic file 20.

The electronic file 20 includes computer readable data that can be processed by a computer processor to perform one or more functions. For example, the electronic file 20 may include information that can be processed by a hardware processor to display a certain text on a screen, render an image, video or audio information, or a combination of any of these functionalities. Computer readable data may be primary data and/or metadata as described below.

The computer readable data in the electronic file may be organized such that it is compliant with various industry standards. For example, the information on the electronic file 20 may be organized to be compliant with the TIFF format. The electronic file 20 also includes self-documenting metadata information as well as additional metadata entered as commentary or as the result of making calculations or reading instrument settings and finally authentication information based on unique identifiers (UIDs) generated from the content, including the primary data and metadata, of the electronic file page as described below.

Figure 2:
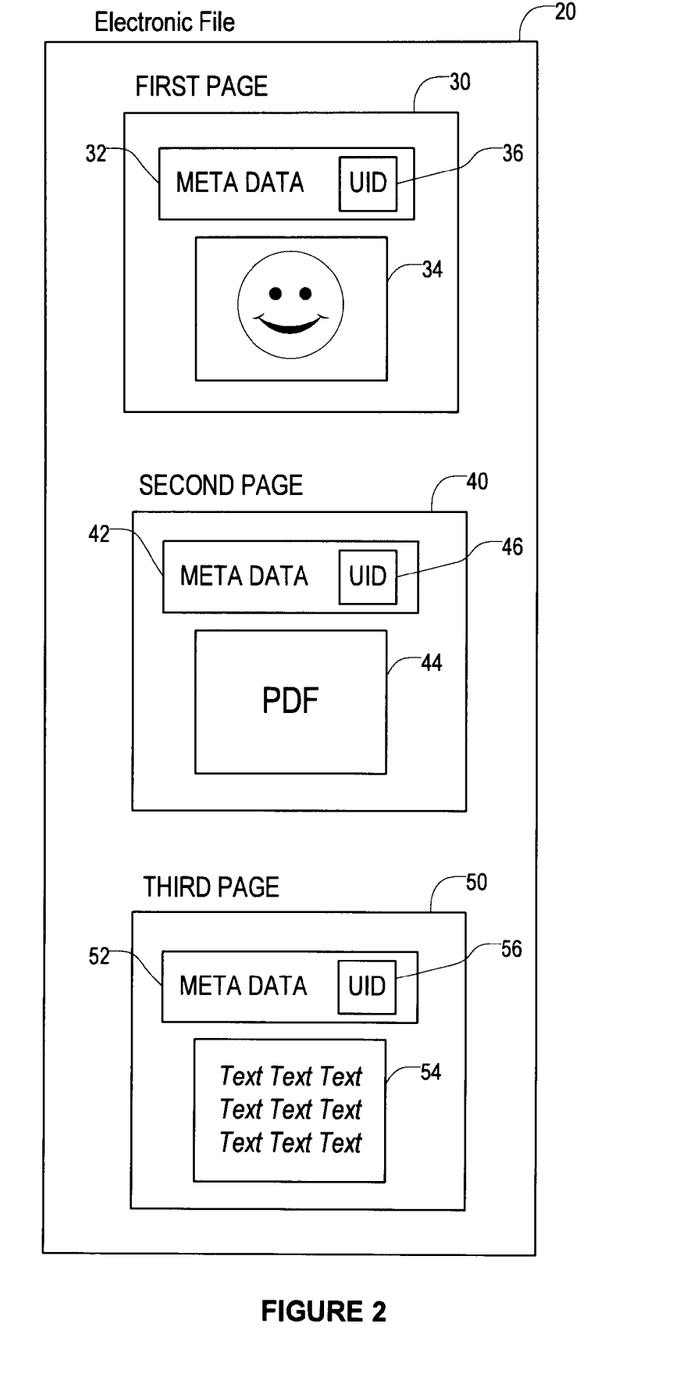
FIG. 2 is a schematic diagram illustrating exemplary contents of the electronic file shown in FIG. 1.

Referring now to FIG. 2, illustrated therein is the exemplary contents of the electronic file 20. The electronic file 20 comprises a first page 30, a second page 40, and a third page 50. In other words, the electronic file 20 includes a :file envelope" and a plurality of pages within the envelope.

The number and the content of pages in other electronic files may be different from that of the electronic file 20. That is, the pages shown in FIG. 2 are only for exemplary purposes. In other embodiments, the number and the content of the pages of the electronic files may differ. Generally, each electronic file 20 contains at least one page and there is no logical limit (except those imposed by operating systems) on the maximum number of pages that can be contained in the electronic file 20.

Each of the pages 30, 40 and 50 contains a page metadata portion and a page primary data portion. As shown, page 30 contains page metadata 32 and page data 34. Similarly, page 40 contains page metadata 42 and page data 44, and page 50 contains page metadata 52 and page data 54.

The page metadata 32, 42, 52 may contain information about the corresponding page data 34, 44, 54. Generally, metadata 32 may include contextualization information associated with the test results. For example, metadata 32 may include descriptions of how the primary data was generated, various interpretations of the primary data and reasons therefore, what the primary data means to either primary or secondary users of the data and so on. It may also contain test version and configuration information.

Page data 34 may be an image from an imaging source such as an X-ray imaging device and the page metadata 32 may contain information about the subject of the medical image (e.g. Patient's name, left/right elbow, clinic's name, family physician information, etc.). In some embodiments page metadata may include annotations, commentary, and area of interests regarding the page data and location (e.g. coordinates) on the page data of such information.

Each type of information stored as part of the metadata 32, 42, 52 may be identified in one embodiment using a tagged metadata format in the form of tag-name/tag-value pairs. An example of the use of this type of tag-name/tag-value pair system is the Tagged Image File Format (TIFF).

The page data 34, 44, and 54 comprises primary data about a subject. Page data 34, 44, and 54 may be different types of data. For example, as shown, page data 34 is an image, page data 44 is a file format specific representation of a file in the Portable Document Format (PDF), and similarly page data 5 is a file format specific representation of a text document originally created using a word processing program. In other embodiments, the page data may simply be an anchor for other forms of non-image data stored as metadata. Forms of non-image data can include but are not limited to executable code and digital audio/video recordings.

Each of the pages 30, 40, 50 also contains globally unique identifier ("UID") 36, 46, 56. Each of the UIDs 36, 46 and 56 is generated based on all of the data-(primary data and metadata) contained in the respective electronic file page. In some cases, the globally unique identifiers may be have a same length.

Figure 4:
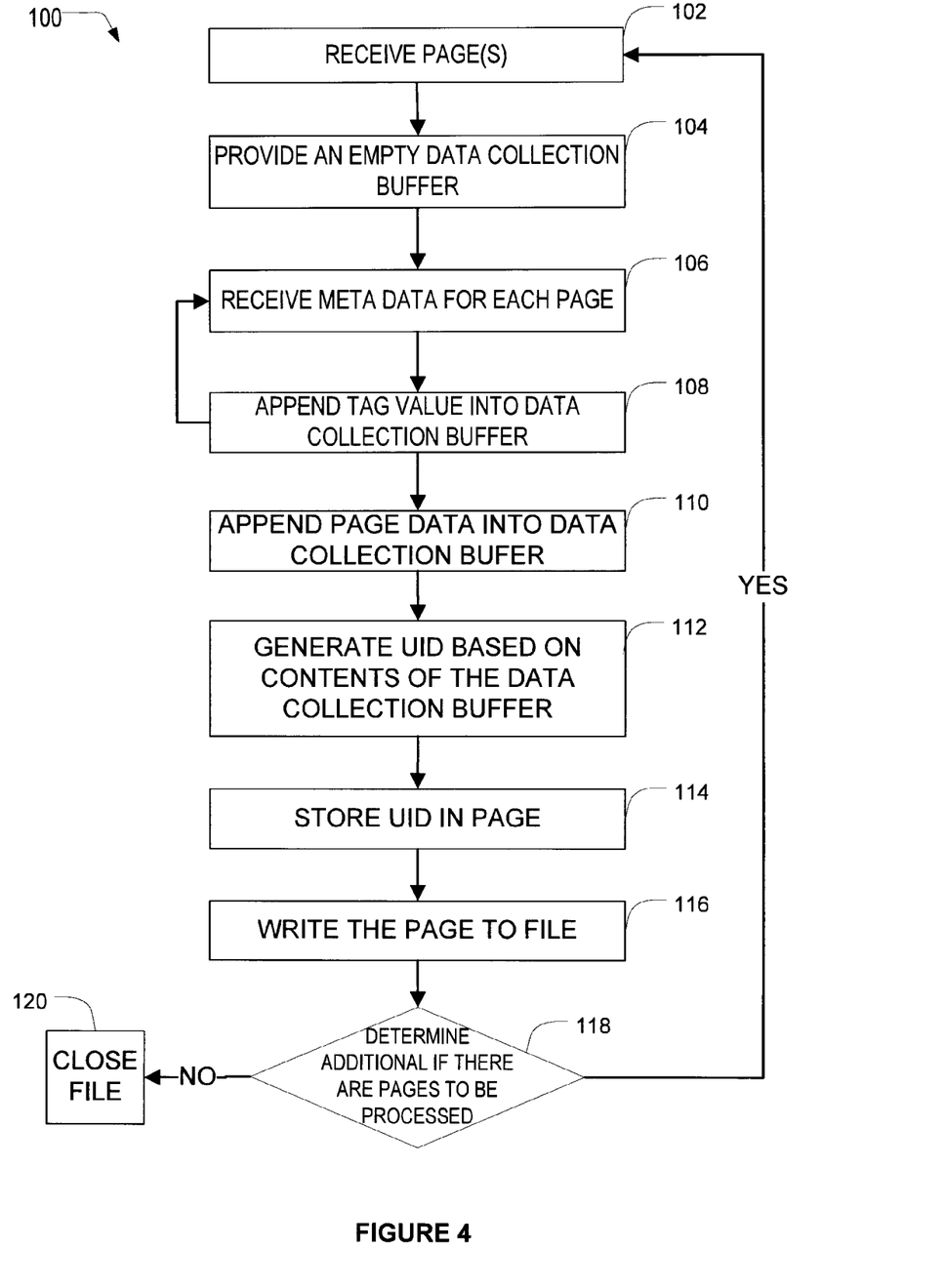
FIG. 4 is a block diagram illustrating steps of a method for generating an electronic file having authentication information according to some embodiments.

Each unique identifier is generated based on the bytes specifying, if for example the standard TIFF format is being used, the metadata tag names, tag types and the tag values and all of the primary data such as a digital image data to be written to a file page. The unique identifiers are generated on a page by page basis. For example, the unique identifier may be generated in accordance with a method such as the method 100 as described herein below. This unique identifier is also calculated without the use of any Public Key Infrastructure technology so that no digital certificates are necessary.

In some cases, tag-specific alphanumeric identifiers may be generated using an algorithm that converts a semantically meaningful but variable length string of a complex dataset (e.g. ASCII characters) representing a tag name into an alphanumeric string of uniform length that also specifies that name. The alphanumeric string of uniform length may be advantageous in that the alpha numeric identifier is can be more efficiently processed for indexing and search purposes. The tag-specific alphanumeric identifiers are unique to each tag name but are not unique globally. These identifiers may be replicated subsequently such that the tags associated with these identifiers may be located.

Figure 3:
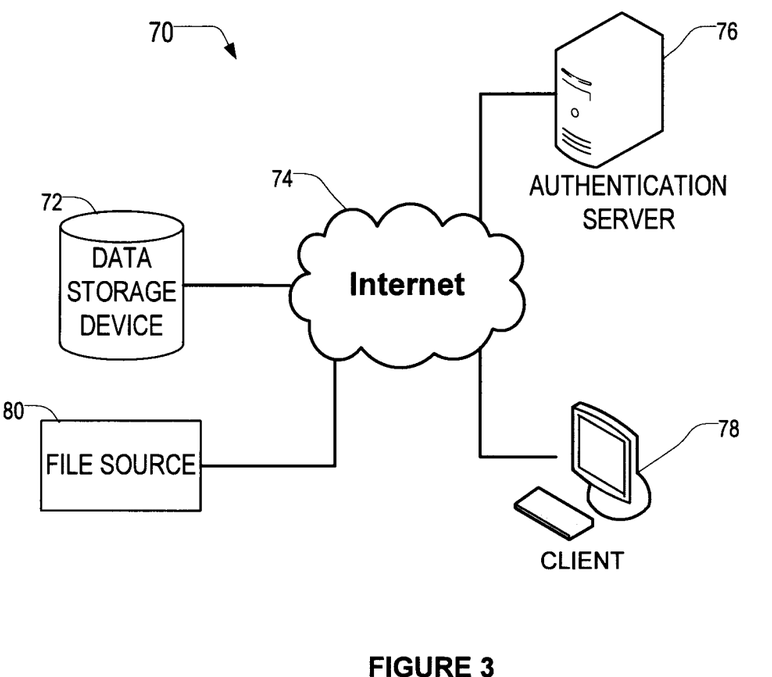
FIG. 3 is a schematic diagram illustrating a system for authenticating electronic files according some embodiments.
Figure 5:
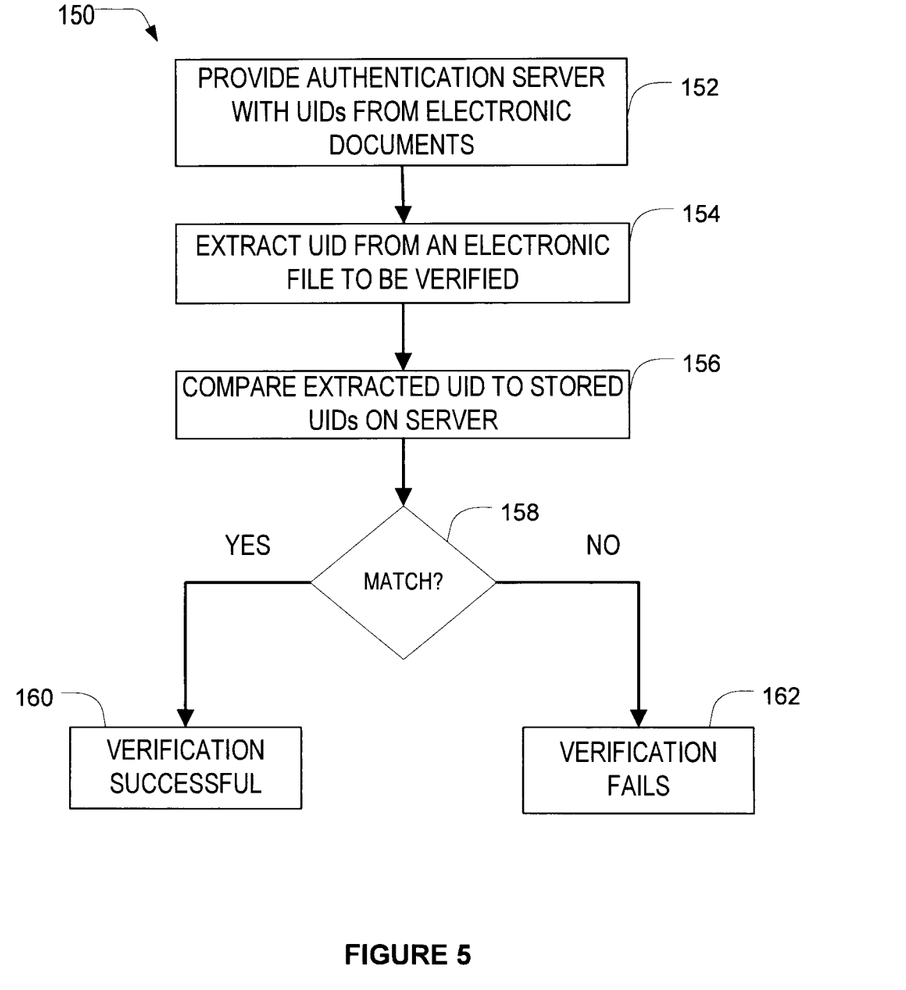
FIG. 5 is a block diagram illustrating steps of a method for authenticating an electronic file according to some embodiments.

The page unique identifier can be used to authenticate the integrity of the contents of each page of the electronic file. For example, the system 70 described herein below illustrates one embodiment wherein the page unique identifier for the electronic file can be used to authenticate the electronic file. In another example, a method such as the method 150 described below can be used to authenticate the electronic file having the unique page identifier.

Because this method is based on enabling a sufficiency of metadata to be recorded, the file pages then become self-documenting or self-describing. In addition because the file is self-authenticating and self-describing, it requires no third party agent or external agency to verify the file.

The embodiments described herein combine elements of digital media file technology and alpha-numeric unique identifier generation to create electronic files that contain authentication information. Generating unique identifiers from the metadata and primary page data contained within a multi-page electronic file and comparing it to the UID previously recorded for that page allows consumers to verify whether the contents of any page of the electronic file have been altered since it was first created.

An electronic file containing this system of unique identifiers has applications in different industries ranging from, but not limited to: medical diagnostics, digital media, military and pharmaceuticals. Each one of these industries will find the unique identifier useful for: digital data authentication; indexing large collections of data using simpler and therefore most cost effective technology; and information search.

By embedding self-authentication unique identifiers on each page of a multi-page digital media electronic file, a permanent link is established between the metadata in a page and the page data. If either is missing or tampered with, the unique identifier cannot be replicated because the input values to the UID generating function will differ from the input values used to generate the original UID.

Each electronic file having unique identifiers embedded in each page of the file can be said to be a self-authenticating electronic file where a self-authenticating file is a file that can be accepted as being what it purports to be without any additional proof. That is, all the information required to ascertain the integrity of the content of the file can be found within that file.

Referring now to FIG. 3, illustrated therein is a system 70 for authenticating files according to another embodiment of the invention.

The system 70 comprises a data storage device 72 connected to a communication network 74 such as the Internet, and through the communication network 74 to the authentication server 76. As shown, the system 70 also includes a file source 80 that generates electronic files that are stored in the data storage device 72 and a client computer 78 that wishes to access the electronic files and authenticate the integrity thereof.

The data storage device 72 may be similar to the data storage device 10 as shown in FIG. 1 and contains at least one electronic file such as electronic file 20.

The file source 80 is in data communication with the data storage device 72 and the authentication server 76. The file source 80, for example, may be an imaging machine that generates an electronic file comprising at least one page having image page data, and associated metadata and UID. The UID value for the page may be reported to the authentication server 76 for authentication purposes as described below.

The authentication server 76 stores the UID values from the electronic files on the data storage device 10. As such, client computer 78 wishing to verify the authenticity of a page data on an electronic file on the data storage device 72 may consult the server 76 to obtain the UID value of the electronic file. The UID value(s) of the electronic file may be uploaded to the server 76 by an authorized source at the time the UID was generated. If the page data of the page has been modified after the UID was generated (for e.g. using method 100 as described herein below), the UID value generated based on the page data would be different from that of the original UID value, which would indicate that the page data of the page has been modified.

System 70 according to this embodiment allows for a network-notarized digital image capture system that can detect tampering of page data captured by the file source 80.

Referring now to FIG. 4, illustrated therein are steps of a method 100 for generating an electronic file having unique identifiers for each page according to another embodiment of the invention.

The method 100 begins at step 102 where a number of pages are received to generate an electronic file. In some embodiments, the electronic file may be similar to the electronic file 20 as described above and each page may be similar to the pages 30, 40, 50 described above.

The method proceeds to step 104, where an empty data collection buffer is provided. If the data collection buffer contains data from previous unique identifier generation iterations, the buffer is reset At step 106, metadata associated with the primary data for each page is received and recorded in the electronic file. As mentioned above, metadata elements could be similar to the tags as described in the official specification of the TIFF format although new tags can be specified as deemed necessary. Some of the metadata elements included may be populated with a null value if they are not applicable to the corresponding page data.

At step 108, as the metadata for each metadata element is recorded in the electronic file, the tag name, tag type and tag value are also appended to the data collection buffer. Once the tag name, type and values for all available tags are populated and appended into the data collection buffer, the method proceeds to step 110.

At step 110, the page data is appended into the data collection buffer. The page data may be a bit stream representing the page data.

At step 112, a UID is generated based on the contents of the data collection buffer. For example, a hash function or any other suitable mathematical function, which meets the criteria presented below, may be used to generate the UID.

The process of generating the unique identifiers that enables this method can be implemented using a variety of mathematical functions that can generate a single value from processing an arbitrarily long data set. The UID generating function may have one or more of the following set of properties: 1) a value can be easily computed given a data set message; 2) given a value, it is infeasible to find the message that produced the value; 3) the value will be changed if the message is changed; and 4) two different message strings will result in different values. The generated value could be an arbitrary string of symbols. For example, a set of alphanumeric characters could be used to represent the value where these characters are selected from Unicode or ASCII set of characters. One example of such a function is MD5 Message-Digest Algorithm.

At step 114, the UID generated is stored in an appropriate metadata element in the page as part of the metadata for the page.

At step 116, the page, including the UID value and corresponding meta tag is written to the electronic file.

At step 118, the method 100 determines whether there are additional pages to be processed. If there are additional pages to be processed, the method returns to step 102. Alternatively, if there are no additional pages to be processed, the method proceeds to step 120 where the electronic file is closed. In some cases, the file can be subsequently re-opened and additional pages may be inserted into the file using the method described above.

In some embodiments, one or more generated UIDs may be provided to an authentication server such that they are available for use to confirm the authenticity of the contents of each page, for example, as described in method 150 below.

Referring now to FIG. 5, illustrated therein is a method 150 to authenticate an electronic file having a unique identifier according to another embodiment of the invention.

The method begins at step 152 wherein an authentication server having one or more electronic files having one or more UIDs is provided. For example, method 100 described above may be applied to the electronic files in the data storage device At step 154, the unique identifier of the electronic file is extracted.

At step 156, the UID is compared to the set of UIDs stored on the authentication server.

At step 158, it is determined whether there is a match between the extracted UID and one of the UIDs stored on the server. If there is a match, the method proceeds to step 160 wherein it is indicated that the electronic file verification is successful. If there is no match, then the method proceeds to step 162 wherein it is indicated that the electronic file authentication has failed.

Figure 6:
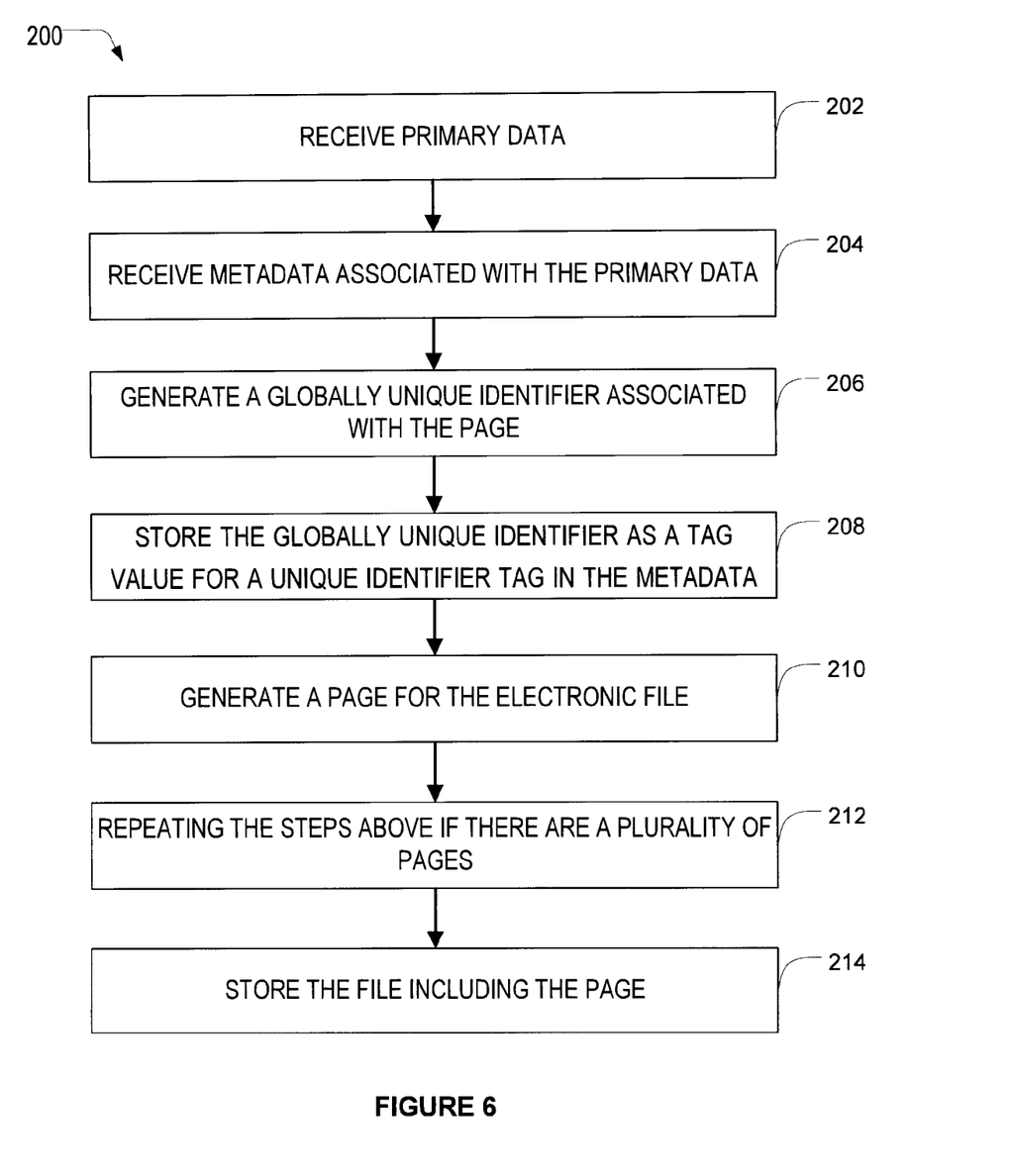
FIG. 6 is a block diagram illustrating steps of a method for generating an electronic file according to some embodiments.

Referring now to FIG. 6, illustrated therein is a method 200 for generating an electronic file according to some other embodiments.

At step 202, primary data for at least one page to be included in an electronic file is received.

At step 204, metadata associated with the primary data is received. The metadata comprising a plurality of tags and corresponding tag values associated therewith.

At step 206, a globally unique identifier associated with the page based upon the primary data and the metadata associated therewith is generated.

At step 208, the globally unique identifier is stored as a tag value for a unique identifier tag in the metadata associated with that page.

At step 210, at least one page for the file is generated. The at least one page comprising the page data and the metadata including the globally unique identifier.

At step 212, if the at least one page comprises a plurality of pages, steps 202-210 are repeated to generate a plurality of the pages for the electronic file.

At step 214, the file comprising the at least one generated page is stored in the repository.

It should be understood that the steps in the methods described herein are for illustrative purposes. In other embodiments, one or more steps may be omitted, performed in a different order, or one or more additional steps may be added.

Embodiments described herein may be used with the TIFF (Tagged Image File Format) standard. The TIFF file format standard uses a tag-name/tag-value format to store metadata as well as image data within the same file page location. The systems and methods described above can be applied to other imaging standards (but not limited to) such as JPEG, PNG, JPEG2000, FITS, DICOM, and other file formats where the image data is accompanied by metadata. While some file formats do not use a tag name/tag value type mechanism to store metadata but rather an address/value scheme, the concept described herein can be applied to these different metadata storage strategies as well. The systems and methods described above can also be applied to databases The systems and methods described above can also be applied to other forms of non-image based information not traditionally stored in image related file formats of this type. For example, computer code can stored as a byte string in those file formats within a metadata element and retrieved in a way that it still executes in the same ways as before it was stored in those image file formats.

The electronic file in some embodiments may be in a format having authentication information for use within biomedical diagnostics and/or biological systems. This embodiment may be referred to as the "BioTIFF" electronic file format.

According to another embodiment of the invention, there is provided a system and method for using electronic files having authentication information in virtual protective product packaging labelling.

There are many situations where such a system and method might be useful. For example, when the object being probed and recorded is a product whose quality or identity needs to be assessed. The way in which products like medicines or diagnostic test kits are generated adds value to the raw material used in their production and allows the distributor of that product to make claims about that value in order to justify the price charged for that product. It also allows users to reliably expect a specific level of utility. These claims are included in the protective product packaging labelling associated with distribution of the product. Virtual protective product packaging labelling enabled by the authentication system described herein facilitates linking diagnosis of material properties to a description of those properties stored in an electronic file.

Although quality claims are often specified on packaging distributed with these products, that packaging can be separated from the product or substituted. Thus, having a way to register additional information about the product, in a way that can be directly ascertained latter at the point-of-use, can help to determine the authenticity of the product. For example, a specific way of imaging material properties of the product can generate a representation at the point-of-use that can be compared to known reference representations of those same imaging results. Alternatively, an index comprising metadata attributes can be used to search for similar representations of know products using fuzzy logic applications.

This system also helps agents or employees responsible for ascertaining product production quality who are generally located some distance from users to assure those users that the product that they have in their possession is the same as the one that the manufacturer claims pertain to.

In some embodiments, the system may be used by a user to determine whether a medical pill that has been received (e.g. from an online pharmacy) is authentic.

To determine whether the pill is authentic, the user could obtain an analytical image of the pill using a customized digital diagnostic device designed to characterize key material properties, such as colour, shape, and chemical spectral patterns characteristic of excipients, active ingredients and/or special chemical taggants of the particular pill as well as reading a UID printed on the pill. There may be many other ways of using a digital diagnostic system to record a sufficiency of signature measures needed to uniquely identify the material at hand. The user would then submit the unique identifier and the set of material properties to the authentication server. The authentication server will compare the unique identifier to the set of know unique identifiers and compare the acquired material properties to expected material properties. If the submitted UID and material properties are as they should be, a message indicating that the pill is authentic is provided to the user. In the alternative, a message indicated that the pill is not authenticated is provided to the user.

There are many other ways in which uncertainty about the identity of the product can arise. In addition, regardless of what the user knows or does not know at the time of use, it can be useful to have an unambiguous record of what instantiation of the product was used or generated at a particular time by recording some of the same identifying features that can be used to determine its similarity to a reference standard at a later date as described above. The claimed system and method allows enough analytical information to be stored with the digital diagnostic recording of the target so that self-authentication is enabled. This means the data can be trusted as being what it appears to be at a level that can bear-up to judicial scrutiny within a court of law. There is sufficient data available within the file envelope to establish that the claim implied by the virtual protective packaging labelling is warranted.

The embodiments described herein may have one or more of the following features.

The embodiments provides a unique identifier for each page within multi-page digital media electronic file calculated using the meta-data and the data.

The electronic file created using the above methods constitutes a repository from which other repositories can be generated. For example an electronic file of this type can, with the appropriate software applied to it generate: a relational database, a searchable index, and so on. The electronic file of this type, then can be made to behave like a database without all the cost associated with operating a relational database.

Applying the unique identifier methodology described above to the domain of information search and indexing may be advantageous. For example searching for specific pages will be sped-up and simplified as the unique identifiers are much easier and simpler to work with than complex semantic identifiers.

Automatic indexing of text generally involves lexical analysis and the filtering of stoplist words. Unfortunately these steps also require processing resources when querying for terms. The additional resources that are required to query for terms are more pronounced in more complicated queries which are implemented by more complicated computer code. This code is required to allow, for example, searches for terms that contain underscores. By applying the function used to generate unique identifiers to metadata that are to be indexed, the query code may be come simpler (less complex), smaller (less lengthy), which may require less resources to process and may be executed in a shorter time (faster).

Use of unique identifiers allows the establishment of a system where, for example, a digital image and all associated metadata are simultaneously captured and stored in a page of a digital electronic file and the unique identifiers are stored not only in the file at hand but also on an external network attached server. The unique identifier system enables creation of a networked-notarized digital image capture system that makes it practically impossible for tampering with the capture of digital media as there need be no delay between the capture event and its registration. By storing the unique identifiers on an external network-attached server, a digital media file authentication service is provided.

The unique identifier can also be used to verify that data held in a relational database has not been altered or tampered. For example each row in a table held in a relational could have an extra column which contains the value of the unique identifier for that row. This unique identifier would be calculated from the row's other data. This extra value would allow a user to determine if any data in the database has been altered.

While the above description provides examples of one or more apparatus, methods, or systems, it will be appreciated that other methods, or systems may be within the scope of the present description as interpreted by one of skill in the art.

The invention claimed is:

1. A method comprising:
associating, at a computing device, primary data with metadata, the metadata comprising a plurality of tags and corresponding tag values associated with the primary data;
generating, at the computing device, an identifier by applying a given algorithm to a combination of the primary data and the metadata, wherein the identifier is calculated as a function of both the primary data and the metadata such that any alteration in one or more of the primary data and the metadata results in a corresponding change to the identifier according to the given algorithm;
incorporating the identifier into the metadata as a tag value; and
storing, at a memory, the primary data with the metadata including the identifier as a page of an electronic file;
repeating the associating, the generating, the incorporating, and the storing steps for further primary data, each of the further primary data stored with respective metadata, including a respective identifier generated using the given algorithm, as a further page of the electronic file;
whereby the identifier can be used to detect tampering with one or more of the primary data and the metadata of the page.

2. The method of claim 1, further comprising storing a copy of the identifier in a location separate from the computing device, at one or more of:
a time when the identifier is generated, and
a later time.

3. The method of claim 1, further comprising:
storing, at one or more of a second memory, the computing device, and another computing device, and separate from the electronic file, a copy of the identifier in an index, the index being searchable so that the primary data and the metadata can be retrieved from the memory using the copy of the identifier found in a search of the index, the storing of the copy of the identifier in the index occurring at one or more of when the identifier is generated and at a later time.

4. The method of claim 3, wherein the index comprises one or more of: a plurality of identifiers of respective primary data; respective metadata; the identifier of the combination of the primary data and the metadata; and, searchable data associated with one or more of the respective primary data and the respective metadata.

5. The method of claim 4, wherein the searchable data comprises one or more of: information associated with the primary data; the metadata tag values; metadata tag names; and respective alphanumeric strings, of uniform length identifying comprising one or more of the metadata tag names, the metadata tag values, converted to the respective alphanumeric strings of uniform length using a common algorithm.

6. The method of claim 1, further comprising:
retrieving the primary data and the metadata from the memory using a copy of the identifier stored separate from the primary data and the metadata;
removing the identifier from the metadata;
after the removing, generating a second identifier by applying the given algorithm to the combination of the primary data and the metadata with the identifier removed, wherein the second identifier is calculated as a function of both the primary data and the metadata such that any alteration in one or more of the primary data and the metadata results in a corresponding change to the second identifier according to the given algorithm;
confirming that the primary data and the metadata have not been changed when the second identifier matches the copy of the identifier.

7. The method of claim 1, wherein the electronic file comprises a repository convertible to one or more of a relational database, a spreadsheet, a Portable Document Format (PDF) file, and another file format for providing one or more of the primary data and the metadata.

8. The method of claim 1, wherein the memory comprises a repository of a plurality of electronic files, each of the plurality of the electronic files comprising one or more respective pages, each of the one or more respective pages comprising associated respective primary data and respective metadata, each of the respective metadata comprising a respective identifier of a combination of the respective primary data and respective metadata, independent of the respective identifier, the repository searchable using a copy of the identifier stored separate from the repository.

9. The method of claim 1, wherein the incorporating the identifier into the metadata as the tag value provides one or more of digital product packaging and virtual protective product packaging.

10. The method of claim 1, wherein one or more of the plurality of tags and the tag values comprise one or more processed byte streams such that the format of the electronic file is preserved, wherein the processed byte stream comprises one or more of a different data type and a same data type as the primary data.

11. The method of claim 1, wherein the primary data comprises one or more of diagnostic data, scanned document data, text data, graphical data, portable document format (PDF) data, TIFF data, JPEG data, PNG data, FITS data, DICOM data, legal data, e-discovery data, medical data, manufacturing data, pharmaceutical data, and production line data.

12. A system comprising:
at least one computing device configured to:
associate primary data with metadata, the metadata comprising a plurality of tags and corresponding tag values associated with the primary data;
generate an identifier by applying a given algorithm to a combination of the primary data and the metadata, wherein the identifier is calculated as a function of both the primary data and the metadata such that any alteration in one or more of the primary data and the metadata results in a corresponding change to the identifier according to the given algorithm;
incorporate the identifier into the metadata as a tag value; and
store, at a memory, the primary data with the metadata including the identifier as a page of an electronic file;
repeat the associate, the generate, the incorporate, and the store steps for further primary data, each of the further primary data stored with respective metadata, including a respective identifier generated using the given algorithm, as a further page of the electronic file;
whereby the identifier can be used to detect tampering with one or more of the primary data and the metadata of the page.

13. The system of claim 12, wherein the at least one computing device is further configured to store a copy of the identifier in a location separate from the computing device, at one or more of:
a time when the identifier is generated, and
a later time.

14. The system of claim 12, wherein the at least one computing device is further configured to:
store, at one or more of a second memory, the computing device, and another computing device, and separate from the electronic file, a copy of the identifier in an index, the index being searchable so that the primary data and the metadata can be retrieved from the memory using the copy of the identifier found in a search of the index, storing of the copy of the identifier in the index occurring at one or more of when the identifier is generated and at a later time.

15. The system of claim 14, wherein the index comprises one or more of: a plurality of identifiers of respective primary data; respective metadata; the identifier of the combination of the primary data and the metadata; and, searchable data associated with one or more of the respective primary data and the respective metadata.

16. The system of claim 15, wherein the searchable data comprises one or more of: information associated with the primary data; the metadata tag values; metadata tag names; and respective alphanumeric strings, of uniform length identifying comprising one or more of the metadata tag names, the metadata tag values, converted to the respective alphanumeric strings of uniform length using a common algorithm.

17. The system of claim 12, wherein the at least one computing device is further configured to:
retrieve the primary data and the metadata from the memory using a copy of the identifier stored separate from the primary data and the metadata;
remove the identifier from the metadata;
after the identifier has been removed from the metadata, generate a second identifier by applying the given algorithm to the combination of the primary data and the metadata with the identifier removed, wherein the second identifier is calculated as a function of both the primary data and the metadata such that any alteration in one or more of the primary data and the metadata results in a corresponding change to the second identifier according to the given algorithm;
confirm that the primary data and the metadata have not been changed when the second identifier matches the copy of the identifier.

18. The system of claim 12, wherein the electronic file comprises a repository convertible to one or more of a relational database, a spreadsheet, a Portable Document Format (PDF) file, and another file format for providing one or more of the primary data and the metadata.

19. The system of claim 12, wherein the memory comprises a repository of a plurality of electronic files, each of the plurality of the electronic files comprising one or more respective pages, each of the one or more respective pages comprising associated respective primary data and respective metadata, each of the respective metadata comprising a respective identifier of a combination of the respective primary data and respective metadata, independent of the respective identifier, the repository searchable using a copy of the identifier stored separate from the repository.

20. The system of claim 12, wherein the incorporating the identifier into the metadata as the tag value provides one or more of digital product packaging and virtual protective product packaging.

21. The system of claim 12, wherein one or more of the plurality of tags and the tag values comprise one or more processed byte streams such that the format of the electronic file is preserved, wherein the processed byte stream comprises one or more of a different data type and a same data type as the primary data.

* * * * *